United States Patent [19]

Nadeau

[11] Patent Number: 4,900,312
[45] Date of Patent: Feb. 13, 1990

[54] INFUSION DEVICE FILTER

[75] Inventor: Michael A. Nadeau, North Attleboro, Mass.

[73] Assignee: C. R. Bard, Inc., Murray Hill, N.J.

[21] Appl. No.: 151,407

[22] Filed: Feb. 2, 1988

[51] Int. Cl.$^4$ .......................................... A61M 5/005
[52] U.S. Cl. ................................................... 604/246
[58] Field of Search ............... 604/148, 246, 201, 905, 604/93, 8–10, 175, 179, 891.1; 138/40, 42, 89.3; 210/321.72

[56] References Cited

U.S. PATENT DOCUMENTS

| | | |
|---|---|---|
| 3,951,147 | 4/1976 | Tucker et al. . |
| 3,958,557 | 5/1976 | Sharp et al. ............................. 604/52 |
| 4,190,048 | 2/1980 | Sampson . |
| 4,266,576 | 5/1981 | Bradford ................................ 138/42 |
| 4,464,178 | 8/1984 | Dalton . |
| 4,484,912 | 11/1984 | Raible ................................ 604/175 |
| 4,496,343 | 1/1985 | Prosl et al. . |
| 4,511,163 | 4/1985 | Harris et al. ......................... 604/905 |
| 4,547,194 | 10/1985 | Moorehead .......................... 604/905 |
| 4,692,147 | 9/1987 | Duggan . |
| 4,762,517 | 8/1988 | McIntyre et al. .................... 604/175 |
| 4,781,681 | 11/1988 | Redmond et al. ................. 604/891.1 |

Primary Examiner—Jerome L. Kruter

[57] ABSTRACT

A filter for an infusion device is formed from only two parts, an opening in the side wall of the device and a shaft secured within the opening. These two parts forming the filter also provide an exit port and a catheter attachment site for the infusion device.

18 Claims, 3 Drawing Sheets 4,900,312

INFUSION DEVICE FILTER

BACKGROUND OF THE INVENTION

This invention relates to subcutaneously implanted infusion devices and in particular to a filter system for such devices.

Subcutaneous infusion devices are totally implantable and are designed to provide repeated access to a body space such as the vascular system. They typically include an injection chamber accessible through a septum, the injection chamber being connected by an exit port and catheter to the desired body space. The device is implanted just beneath the skin, and the injection chamber may be accessed repeatedly by passing a needle through the skin and septum.

One such device is known as an infusate pump. An infusate pump has a relatively large reservoir for storing a supply of medicament. The medicament is pumped from the reservoir to the desired body space at a selected rate. To avoid having to operate on a patient to remove the infusate pump to refill it periodically, the reservoir is accessible through a septum in the wall of the implanted infusate pump.

Another such device is an injection port. An injection port typically includes a relatively small injection chamber accessible through a septum and in direct fluid communication with a body space. The medicament delivered to the injection chamber of the implanted port flows immediately to the body space. Fluid also may be withdrawn from the injection chamber. Injection ports may be very small, as for example the low-profile microinjection port described in the commonly-owned co-pending patent application of even date and entitled MICROINJECTION PORT, Ser. No. 07/151,406.

It is desirable to use a filter in an implantable subcutaneous infusion device to prevent particles introduced into the device's chamber from entering into the body space accessed by the chamber. For example, particles of fat, skin, dust, rubber and plastic sometimes are introduced into the injection chamber of the device as a needle is passed into and through the skin and septum to access the chamber. Such particles may pose a serious danger to the patient, which danger is of increased concern in pediatric patients whose relatively smaller body passages may become blocked more easily than the larger passages of adults.

Conventional membrane-type filters are of limited usefulness in infusion devices. They suffer from questionable compatibility with many of the drugs and fluids that must be delivered; they also may tear or be pierced by a needle. Alternatives to membrane-type filters include filter elements such as screens or plates with small holes. However, manufacturing, manipulating, and attaching such small separate filter elements can be problematic, especially when manufacturing a filter for a low profile device, such as the micro-injection port described in the previously mentioned, commonly owned, co pending patent application.

SUMMARY OF THE INVENTION

The filter system of the invention prevents particles introduced into the injection chamber of the infusion device from entering the body. The filter is formed from only two parts, an opening in the side wall of the device and a shaft secured within the opening. A first portion of the shaft is sized to sealingly mate with the opening and a second portion of the shaft has a cross-sectional area less than the cross-sectional area of the opening at or close to the inside surface of the side wall. The second portion of the shaft and the opening define a space. The smallest cross-sectional area of this space defines the filter. The space communicates with an exit bore through the shaft such that fluid introduced into the injection chamber may exit the injection chamber by passing into the space and out the exit bore.

Preferably the shaft includes a barbed portion which extends from the side wall of the device and acts as a catheter attachment site. Thus, the shaft and the opening in the side wall of the housing together act as a filter, an exit port and a catheter attachment site.

It is an object of the invention to provide a filter system for an infusion device that is easy to manufacture and has few parts.

DETAILED DESCRIPTION OF THE DRAWINGS

The filter system of the invention will be described in connection with a side-entry microinjection port, which port is the subject of a commonly owned patent application of even date and entitled MICRO-INJECTION PORT. The disclosure of that patent application is incorporated herein by reference. It should be understood, however, that the filter system of this invention may be used in virtually any injection port or in other infusion devices, such as for example an infusate pump.

Figure 1:
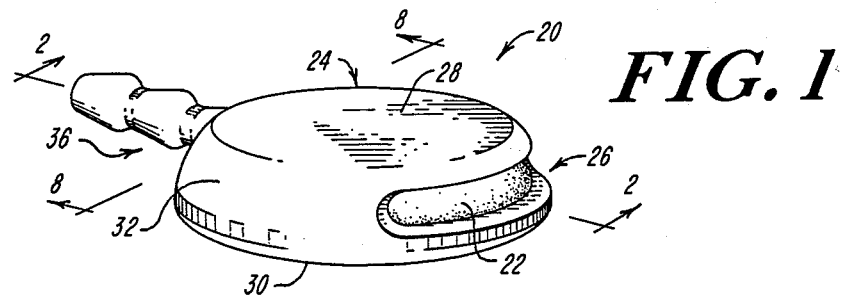
FIG. 1 is a side elevated view of the preferred embodiment of the invention.
Figure 2:
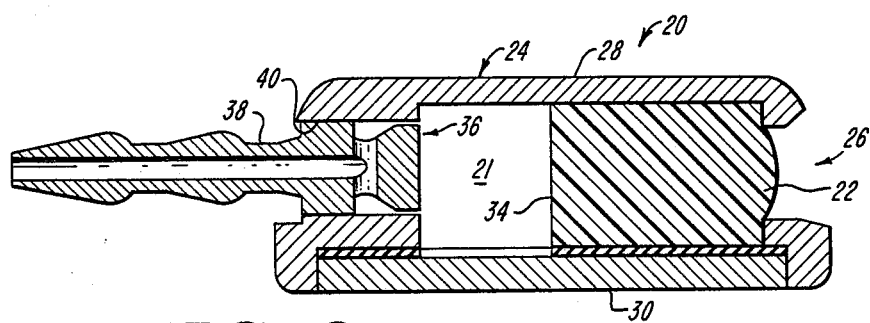
FIG. 2 is a cross-sectional view along lines 2—2 of FIG. 1.

Referring to FIGS. 1 and 2, the side-entry injection port 20 has a housing 24 shaped substantially like a disk. The housing 24 is made of a rigid material, such as metal, and defines an internal injection chamber 21 accessible through an opening 26 in the housing 24, which opening 26 is sealed by the septum 22. A biocompatible metal is preferred over plastic because a metal housing generally requires thinner walls to achieve the desired rigidity and compression on the septum. An implant grade Titanium alloy has been used successfully.

The housing 24 preferably has flat, parallel disk-shaped top and bottom walls, 28 and 30, respectively, which walls are connected along their periphery by a side wall 32. The top and bottom walls 28, 30 are concentric, with the top wall 28 somewhat smaller than the bottom wall 30. The side wall 32 slopes gently from the periphery of the top wall 28 to the periphery of the bottom wall 30. Preferably, the device has rounded corners to minimize tissue irritation when implanted. The top, bottom and side walls 28, 30, 32 along with chamber-facing surface 34 of the septum 22 together define the injection chamber 21.

The opening 26 is in the side wall 32 of the housing 24 and is sealed off by the septum 22. The opening 26 extends approximately 80° around the circular side wall 32. The remainder of the side wall 32 is solid, except for an exit port 36, which exit port provides a filter and an exit path for fluid introduced into the injection chamber 21.

The exit port 36 communicates with the injection chamber 21 and is located in the side wall 32 opposite the septum 22. The exit port 36 in the preferred embodiment is defined by a port outlet connector 38 fitted into a bore 40 in the side wall 32 of the housing 24. The port outlet connector 38 may be made of the same biocompatible material as the housing to facilitate the attachment of the port outlet connector 38 to the housing. Other materials, however, may be substituted. The port outlet connector 38 and the bore 40 in the side wall 32 together serve as a filter system, an exit port and a catheter attachment site for the side-entry injection port 20.

Figure 3:
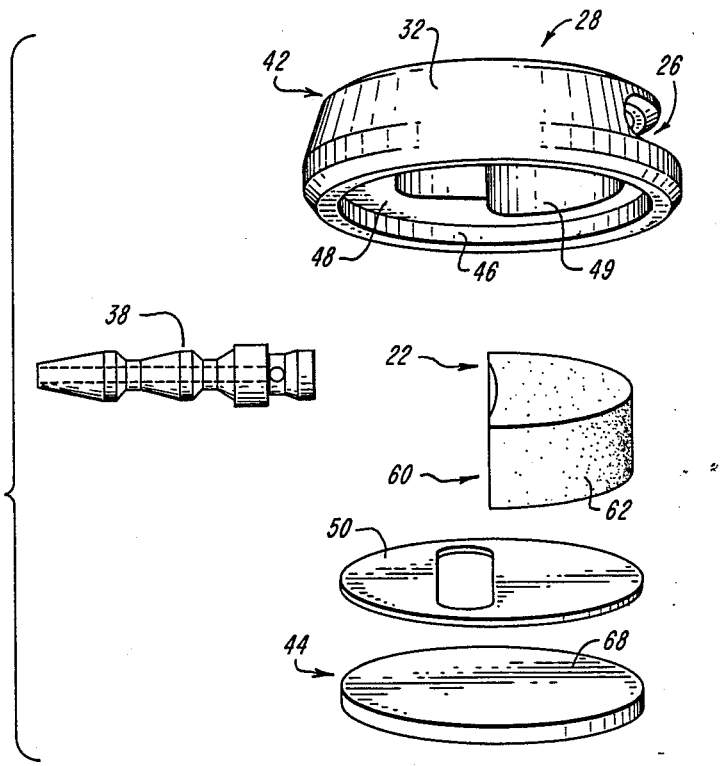
FIG. 3 is an exploded view of FIG. 1.

The injection port 20 including the filter system of the invention is shown in an exploded view in FIG. 3. The rigid housing 24 is constructed from two separate elements, a top element 42 and a bottom element 44. The top element 42 defines the top wall 28 and the side wall 32 of the injection port 20. A lip 46 extends about the periphery of the side wall 32 to form a seat or step 48 also extending completely about the periphery of the side wall 32. The step 48 is parallel to the top wall 28 and is provided to mate in face-to-face relation with the bottom element 44 when the device is assembled. The bottom element 44 is sized to fit just within the lip 46.

The top and bottom elements 42, 44 capture a gasket 50 and the septum 22. The gasket 50 is sized to fit within the lip 46 and between the facing surfaces of the bottom element 44 and the step 48. The gasket 50 is essentially a silicone rubber ring and is captured between the top and bottom elements to form a leak-proof seal.

Figure 4:
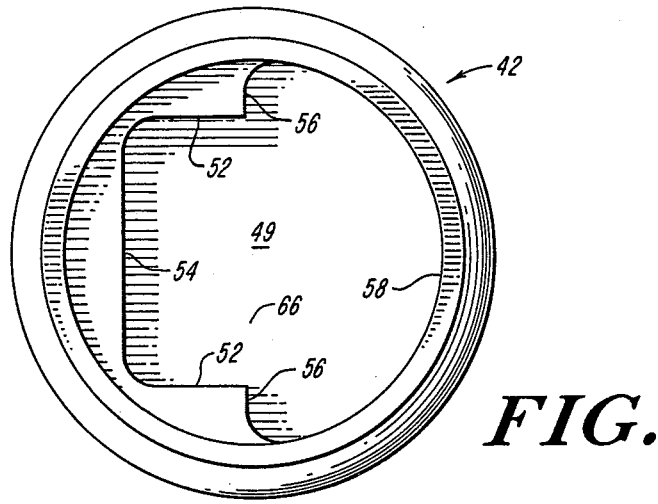
FIG. 4 is a bottom view of the top element of FIG. 3.

The top element 42 has a hollowed out center 49. Referring to FIG. 4, the hollowed out center has a neck region and a head region. The neck region has neck side walls 52 connected at one end by a neck base wall 54. The head region defines a shape similar to a semicircle. The head region has two shoulder walls 56, one each extending perpendicularly from each of the neck side walls 52, and has an arcuate front wall 58 connecting the free ends of the shoulder walls 56.

The septum 22 is sized to fit compressively within the head region. Referring to FIG. 3, the septum also is shaped similar to a slice of a disk, having a chamber-facing wall 60 and an arcuate septum front wall 62. The septum front wall 62 mates with the arcuate front wall 58 of the head region and the ends of the chamber-facing wall 60 mate with the shoulder walls 56 of the head region.

Figure 5:
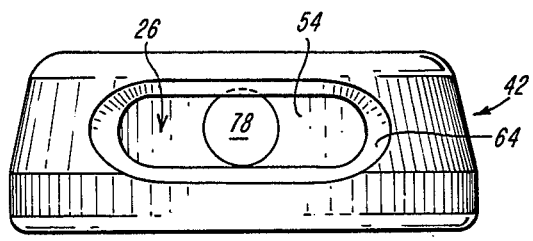
FIG. 5 is a front view of the top element of FIG. 3.

The opening 26 in the top element 42 is shown in detail in FIG. 5. The opening 26 has a beveled edge 64. It is centered relative to the arcuate front wall 58 and is located directly across from the neck base wall 54. The exit port 36 is located and centered in the neck base wall 54.

When assembled, the top and bottom elements 42, 44 compressively capture the gasket 50 and the septum 22. The bottom element 44 is provided with a chamfer (not shown) so that it may be interference fit together with the top element 42. The neck side and neck base walls 52, 54 together with the chamber-facing surface 34 of the septum 22 define the side walls of the injection chamber 21. The inside surface 66 of the top wall 28 and the inside-facing surface 68 of the bottom element 44 form the top and bottom walls of the injection chamber 21.

When used in pediatric patients, the side-entry injection-port 20 has a height of about ⅜" (0.375") or less. In the embodiment described, the height is about 0.225".

Figure 6:
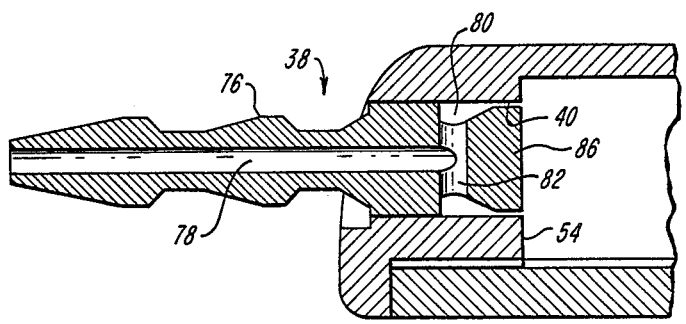
FIG. 6 is an enlarged view of the exit port region of FIG. 2.
Figure 7:
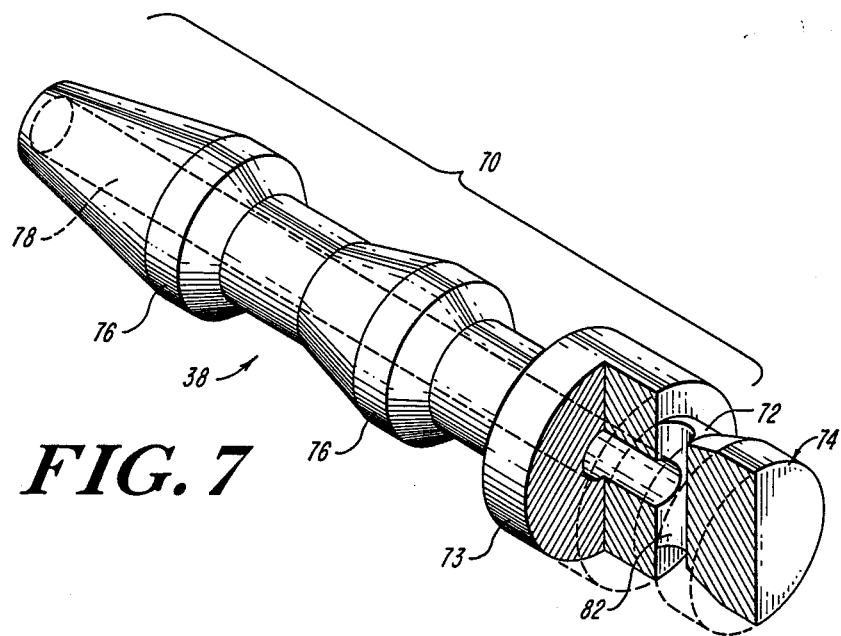
FIG. 7 is an enlarged cross sectional view of the port outlet connector of FIGS. 2 and 3.

As discussed above, the port outlet connector 38 and the bore 40 in the housing 24 define a combination filter system, exit port and catheter attachment site. Referring to FIGS. 6 and 7, the port outlet connector 38 is a cylindrical shaft having a main body 70, a neck 72 and a head 74. The end of the main body 70 meeting neck 72 is a straight cylinder 73 and is sized to fit snugly in the cylindrical bore 40 in the housing 24. The remaining portion of the main body 70 extends from the housing 24 and has conventional barbs 76 for attaching a catheter (not shown). An axial bore 78 extends centrally through the main body 70 of the port outlet connector 38 from the barbed end to the neck 72.

The head 74 also is a straight cylinder. The neck 72 defines a tapering cylinder, with the larger end meeting the head 74. The head 74 and neck 72 have a smaller diameter than that of the cylindrical bore 40 in the housing 24 into which they fit. The walls of the cylindrical bore 40 in the housing 24 and the head and neck 72, 74 define an annular space 80 communicating with the injecting chamber 21. This annular space 80 also communicates with the axial bore 78 in the main body 70 via a transverse bore 82 through the neck 72. Thus, fluid injected into the injection chamber 21 flows through the annular space 80, into the transverse bore 82, then into the axial bore 78 and finally into the catheter (not shown). The catheter delivers the fluid to the appropriate body location.

Figure 8:
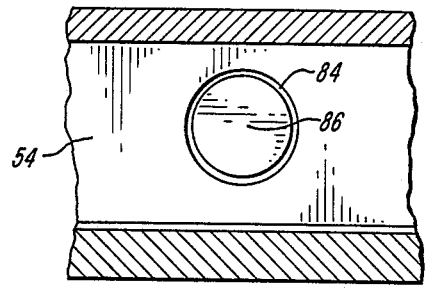
FIG. 8 is a cross-sectional view along lines 8—8 of FIG. 1.
Figure 9:
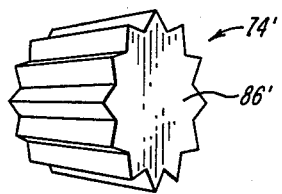
FIG. 9 is a side view of the head and neck region of another embodiment of the port outlet connector of the invention.
Figure 10:
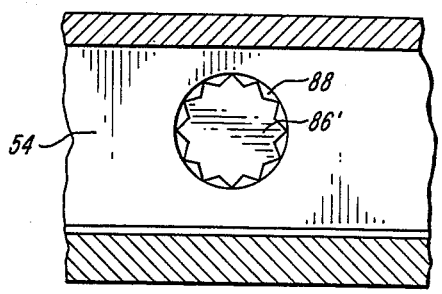
FIG. 10 is a cross-sectional view similar to FIG. 8 using the device of FIG. 9.

Referring to FIG. 8, the filter space 84 between the terminal end 86 of the head 74 and the neck base wall 54 of the injection chamber 21 defines the injection port filter. The terminal end 86 of the head 74 is positioned flush with the neck base wall 54 of the injection chamber 21. The peripheral surface of the terminal end 86 of the connector head 74 may be smooth such that the filter space 84 is an open ring. Alternatively, as shown in FIG. 9 the peripheral surface of the terminal end 86' of the head 74' may be notched so that a ring of holes 88 (FIG. 10) rather than an open ring defines the filter.

Preferably the cross sectional filter area (the area of the ring shown in FIG. 8 or the sum of the area of the individual holes shown in FIG. 10) is greater than the cross sectional area of the exit and delivery path (the smaller of the transverse bore, the axial bore and the catheter inside diameter). Fluid restriction is removed under these conditions. If the cross-sectional filter area is less than the cross-sectional area of the exit and delivery path, then preferably the walls of the head 74 and neck 72 taper quickly from the terminal end 86 of the head 74 to relieve fluid restriction.

In the embodiment described, the port outlet connector 38 is welded to the bore 40, the weld having a maximum width 0.050". The welded assembly does not leak air when tested at 45 PSI for 5 seconds.

The filter of the invention is extremely simple to manufacture as only two parts are required. It is particularly useful for the small side-entry injection port because it eliminates many of the difficulties involved with manufacturing, manipulating and attaching a small, separate part. In particular, it eliminates manufacturing and attaching a small filter as a separate element of the injection port. It should be understood, however, that the filter may be used in any injection port regardless of size and further may be useful in devices other than injection ports.

Various changes and modifications to the embodiments shown in the drawings and described above may be made within the scope of the invention. It, therefore, is intended that all matter contained in the above description and shown in the accompanying drawings shall be interpreted in an illustrative and not limiting sense.

What is claimed is:

1. An implantable subcutaneous infusion device comprising,
    a housing with a rigid wall having an inside surface and a chamber,
    a filter for preventing particles introduced into said chamber from leaving said chamber, said filter including an opening through said wall of said housing, said opening defining a surface, a shaft secured within said opening, a first portion of said shaft sized to sealingly mate with said surface defined by said opening and a second portion of said shaft having a cross-sectional area less than the cross-sectional area of said opening at and close to the inside surface of said wall, said second portion of said shaft and said opening defining a space through which fluid may flow and a bore through said shaft communicating with said space.

2. A device as defined in claim 1 wherein said bore comprises a transverse bore in said second portion communicating with said space, and, an axial bore in said first portion communicating with said transverse bore.

3. A device as defined in claim 1 wherein said shaft has third portion extending from said housing, and wherein said third portion is barbed and comprises a catheter attachment means.

4. A device as defined in claim 1 wherein said opening is a cylindrical bore and said second portion is sized such that a cross-section of said space defines an open ring.

5. A device as defined in claim 1 wherein said opening is a cylindrical bore and said second portion is of a notched configuration such that a cross-section of said space defines a ring of discrete openings.

6. A device as defined in claim 1 wherein the smallest cross-sectional area of said space is greater than the smallest cross-sectional area of said bore.

7. A device as defined in claim 1 wherein the second portion of said shaft defines a cylinder of tapering diameter, the large end of said tapering cylinder directed toward the chamber.

8. An implantable subcutaneous infusion device comprising,
    a housing with a rigid wall and chamber, and
    a filter for preventing particles introduced into said chamber from leaving said chamber, said filter including a cylindrical bore defining an opening through said wall, a shaft secured within said opening, a first portion of said shaft sealingly mating with said opening, a second portion of said shaft having a cross-sectional area less than the cross-sectional area of said opening at and close to the inside surface of said wall, said second portion of said shaft and said opening defining an open space, through which fluid may flow and a third portion of said shaft extending from said housing, said third portion being barbed on its outside surface to facilitate attachment of a catheter, and a bore through said shaft communicating with said space.

9. A device as defined in claim 8 wherein said bore comprises a transverse bore in said second portion communicating with said space, and an axial bore in said first and third portions communicating with said transverse bore.

10. An implantable subcutaneous injection port having a combination filter-catheter attachment site comprising,
    a housing having rigid walls defining an injection chamber accessible through a septum,
    a cylindrical bore defining an opening through one of said walls,
    a shaft secured within said opening, a first portion of said shaft mating sealingly with said opening, a second portion of said shaft having a cross-sectional area less than the corresponding cross-sectional area of said opening at and close to the inside surface of said wall, said second portion having a terminal end lying flush with the inside surface of said one of said walls, and said second portion of said shaft and said opening defining an annular space through which fluid may flow, and a third portion of said shaft extending from said housing, said third portion sized to accept a catheter, and
    an exit bore through said shaft communicating with said annular space, whereby fluid introduced into said injection chamber may pass into said space and out through said exit bore.

11. In an implantable subcutaneous infusion device having a housing with a rigid wall and a chamber, a filter for preventing particles introduced into said chamber from leaving said chamber comprising,
    an opening in said wall of said housing,
    a shaft secured within said opening, a first portion of said shaft sized to sealingly mate with said opening and a second portion of said shaft having a cross-sectional area less than the cross-sectional area of said opening at and close to the inside surface of said wall, said second portion of said shaft and said opening defining an open space through which fluid may flow, and
    a bore through said shaft communicating with said space, and wherein the second portion of said shaft defines a cylinder of tapering diameter, the large end of said tapering cylinder directed toward the chamber.

12. An implantable subcutaneous infusion device comprising,
    a housing with a rigid wall and a chamber, and
    a filter for preventing particles introduced into said chamber from leaving said chamber, said filter including an opening through said wall of said housing, a shaft secured within said opening, a first portion of said shaft sized to sealingly mate with said opening and a second portion of said shaft having a cross-sectional area less than the cross-sectional area of said opening at and close to the inside surface of said wall, said second portion of said shaft and said opening defining an open space through which fluid may flow, and a bore through said shaft communicating with said space, wherein said second portion of said shaft is adjacent to the chamber and said first portion is closely spaced therefrom.

13. A device as claimed in claim 12 wherein said bore comprises a transverse bore in said second portion communicating with said space, and, an axial bore in said first portion communicating with said transverse bore.

14. A filter as defined in claim 13 wherein said shaft has a third portion extending from said housing, and wherein said third portion is barbed and comprises a catheter attachment means.

15. A filter comprising:
a body having an opening defining a surface;
a plug attached to the body and mounted in the opening, the plug having a periphery, at least a portion of which periphery is spaced slightly from at least a portion of the surface of the opening, the spacing between the surface of the opening and the periphery of the plug being sufficiently small as to define a filter for preventing particles of predetermined size from passing therethrough, and wherein the plug has a plurality of grooves formed about its periphery, the plug being constructed and arranged to be mounted in the body opening so that the grooves cooperate with the surface of the opening to define a plurality of passages.

16. A filter comprising:
a body having an opening defining a surface, the opening being a right cylinder;
a plug attached to the body and mounted in the opening, the plug being a shaft including a first portion and a second portion, the second portion having a periphery, at least a portion of which periphery is spaced slightly from at least a portion of the surface of the opening, the spacing between the surface of the opening and the periphery of the plug being sufficiently small as to define a filter for preventing particles of predetermined size from passing therethrough, and an exit bore through the first portion communicating with the spacing defining the filter.

17. A filter comprising:
a body having an opening defining a surface;
a plug mounted in the opening, the plug having a periphery, at least a portion of which periphery is spaced slightly from at least a portion of the surface of the opening to define an open space through which fluid may flow, the spacing between the surface of the opening and the periphery of the plug being sufficiently small as to define a filter for preventing particles of predetermined size from passing therethrough; and
an exit bore through the plug and communicating directly with the space.

18. A filter as claimed in claim 16 wherein said plug defines a cylinder of tapering diameter.

* * * * *